United States Patent
Han et al.

(10) Patent No.: US 12,399,165 B2
(45) Date of Patent: Aug. 26, 2025

(54) ON-LINE CORE HOLDER DESIGN FOR POLYMER QUALITY TESTING DEVICE

(71) Applicant: SAUDI ARABIAN OIL COMPANY, Dhahran (SA)

(72) Inventors: Ming Han, Dhahran (SA); Jinxun Wang, Dhahran (SA); Abdulaziz AlKhateeb, AlKhobar (SA); Abdulkareem AlSofi, Dhahran (SA)

(73) Assignee: SAUDI ARABIAN OIL COMPANY, Dhahran (SA)

( * ) Notice: Subject to any disclaimer, the term of this patent is extended or adjusted under 35 U.S.C. 154(b) by 314 days.

(21) Appl. No.: 18/193,787

(22) Filed: Mar. 31, 2023

(65) Prior Publication Data

US 2024/0329027 A1 Oct. 3, 2024

(51) Int. Cl.
| | |
|---|---|
| *G01N 11/00* | (2006.01) |
| *E21B 43/12* | (2006.01) |
| *G01N 1/20* | (2006.01) |
| *G01N 15/08* | (2006.01) |
| *G01N 33/24* | (2006.01) |

(52) U.S. Cl.
CPC .......... *G01N 33/24* (2013.01); *E21B 43/121* (2013.01); *G01N 1/2035* (2013.01); *G01N 15/0826* (2013.01); *G01N 2001/2064* (2013.01)

(58) Field of Classification Search
CPC .. G01N 1/00; G01N 1/02; G01N 1/20; G01N 1/2035; G01N 11/00; G01N 15/08; G01N 15/0826; G01N 15/15; G01N 33/24; G01N 2001/2064; E21B 43/121
See application file for complete search history.

(56) References Cited

U.S. PATENT DOCUMENTS

| | | | | |
|---|---|---|---|---|
| 3,380,531 | A | * | 4/1968 | Mcauliffe ................ C09K 8/60 166/371 |
| 5,297,420 | A | | 3/1994 | Gilliland et al. |
| 5,493,226 | A | | 2/1996 | Honarpour et al. |
| 8,356,510 | B2 | | 1/2013 | Coenen |

(Continued)

FOREIGN PATENT DOCUMENTS

| | | | |
|---|---|---|---|
| CN | 202832449 U | | 3/2013 |
| CN | 206609667 U | * | 11/2017 ............... G01N 1/20 |

(Continued)

OTHER PUBLICATIONS

CN-206609667-U Machine Translation (Year: 2017).*

(Continued)

*Primary Examiner* — Nguyen Q. Ha
(74) *Attorney, Agent, or Firm* — Osha Bergman Watanabe & Burton LLP (57) ABSTRACT

A removable apparatus having a core holder body and a core sample assembly fitted inside the core holder body is disclosed. The core sample assembly includes a core sample and a sleeve fitted around the core sample. A first flanged stopper and a second flanged stopper are positioned at opposite axial ends of the core holder body. A flow path is formed through the first and second flanged stoppers and interfaces at opposite end surfaces of the core sample. Also provided are an assembly and a system comprising the removable apparatus for use in oilfield applications. Further, a method of testing a property of a fluid using the removable apparatus is provided.

20 Claims, 5 Drawing Sheets

(56) References Cited

U.S. PATENT DOCUMENTS

| | | |
|---|---|---|
| 9,482,631 B2 | 11/2016 | Yang et al. |
| 9,714,889 B2 | 7/2017 | Favero |
| 10,551,290 B2 | 2/2020 | Quillien et al. |
| 10,845,291 B2 | 11/2020 | Kanj et al. |
| 2010/0126266 A1 | 5/2010 | Coenen |
| 2010/0154529 A1* | 6/2010 | Terabayashi ............ E21B 47/10 |
| | | 73/152.27 |
| 2018/0003606 A1 | 1/2018 | Erdmann et al. |
| 2018/0017469 A1* | 1/2018 | English .............. G01N 33/2835 |
| 2021/0302280 A1 | 9/2021 | Al-Qasim et al. |
| 2023/0288305 A1* | 9/2023 | AlKhateeb ............. G01N 11/02 |

FOREIGN PATENT DOCUMENTS

| | | |
|---|---|---|
| CN | 112727416 A | 4/2021 |
| CN | 113791015 A | 12/2021 |
| WO | 2016142623 A1 | 9/2016 |

OTHER PUBLICATIONS

Bonnier, J. et al., "Inline Viscosity Monitoring of Polymer Solutions Injected in Chemical Enhanced Oil Recovery Processes", SPE-165249-MS, Society of Petroleum Engineers, Jul. 2013, pp. 1-9 (9 pages).

Dupas, A., et al., "Impact of Polymer Mechanical Degradation on Shear and Extensional Viscosities: Towards Better Injectivity Forcasts in Polymer Flooding Operations", SPE-164083, Society of Petroleum Engineers, Apr. 2013, pp. 1-11 (11 pages).

Puls, Christopher, et al., "Mechanical Degradation of Polymers During Injection, Reservoir Propagation and Production—Field Test Results 8 TH Reservoir, Austria", SPE-180144-MS, Society of Petroleum Engineers, Jun. 2016, pp. 1-16 (16 pages).

"WellMaster All-In-One Deepwater System", Product Brochure, Weatherford, Access Date: Mar. 30, 2023, URL: <https://www.weatherford.com/documents/brochure/products-and-services/drilling/wellmaster-all-in-one-deepwater-system/> (1 page).

* cited by examiner

ON-LINE CORE HOLDER DESIGN FOR POLYMER QUALITY TESTING DEVICE

BACKGROUND

Enhanced oil recovery (EOR) methods may be used to extract oil from a reservoir that may not otherwise be extractable using conventional primary and secondary methods of oil recovery. EOR operations generally include injecting a fluid (e.g., a gas, a polymer solution, or a liquid) down an injection well to improve oil displacement or fluid flow in the reservoir. Examples of types of EOR operations include chemical flooding (e.g., micellar polymer flooding or alkaline-surfactant-polymer flooding), miscible displacement (e.g., injection of a miscible gas such as $CO_2$, hydrocarbon gases, or mixtures thereof), and thermal recovery (e.g., a steamflood or in-situ combustion).

EOR injectants may be designed to provide selected wetting characteristics in the formation in order to improve recovery of hydrocarbons from the formation. For example, a polymer solution may be designed (e.g., including polymer amount, polymer chain lengths, and polymer type) for a chemical flooding operation to achieve a desired performance downhole, such as to effect downhole pressure, pore channel plugging, wettability, viscosity, and interfacial properties. Changes in the polymer solution composition (e.g., from polymer degradation or harsh downhole environments) may affect the overall EOR operation performance.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

In one aspect, embodiments disclosed herein relate to a removable apparatus. The removable apparatus includes a core holder body and a core sample assembly fitted inside the core holder body, the core sample assembly including a core sample and a sleeve fitted around the core sample, wherein the sleeve is sealed to an inner surface of the core holder body at opposite axial ends of the sleeve. A first flanged stopper and a second flanged stopper may be positioned at opposite axial ends of the core holder body, wherein a flow path is formed through the first and second flanged stoppers and interfaces with opposite end surfaces of the core sample, and wherein the flow path has a diameter that is at least 90 percent of the opposite end surfaces.

In another aspect, embodiments disclosed herein relate to an assembly including a bypass line having a first connection end and a second connection end; a device base positioned along the bypass line, wherein the device base has a first opening to the bypass line, a second opening to the bypass line, and a support structure supporting at least one of the first and second openings; and a removable apparatus as described herein connected to the device base.

In another aspect, embodiments disclosed herein relate to a system including a flow line fluidly connecting an injection pump to a wellhead; a production line fluidly connected to the wellhead; a flow divider valve positioned along the flow line between the injection pump and the wellhead; and a bypass line extending from the flow divider valve to a downstream connection to the production line. An upstream valve and a downstream valve may be positioned along the bypass line, and a device base may be positioned along the bypass line between the upstream valve and the downstream valve. The device base may include a first opening to the bypass line; a second opening to the bypass line; and a support structure supporting at least one of the first and second openings. A removable apparatus may be installed in the device base fluidly connecting the first opening to the second opening The removable apparatus may include a core holder body and a core sample assembly fitted inside the core holder body, the core sample assembly including a core sample and a sleeve fitted around the core sample, wherein the sleeve is sealed to an inner surface of the core holder body. At least one first annular component and at least one second annular component may be positioned at opposite axial ends of the core holder body, wherein a flow path is formed through the at least one first annular component and the at least one second annular component and interfaces with opposite end surfaces of the core sample.

In yet another aspect, embodiments disclosed herein relate to a method that includes providing a device base positioned along a bypass line extending between a flow line to a wellhead and a production line from the wellhead. A removable apparatus may be installed in the device base by connecting a first end of the removable apparatus to a first opening to the bypass line and connecting a second end of the removable apparatus to a second opening to the bypass line to fluidly connect the first opening to the second opening. The method may further include flowing a fluid through the flow line and the bypass line to the removable apparatus and testing a property of the fluid after it flows through the removable apparatus.

Other aspects and advantages of the claimed subject matter will be apparent from the following description and the appended claims.

DETAILED DESCRIPTION

Embodiments of the present disclosure are described below in detail with reference to the accompanying figures. In the following detailed description, numerous specific details are set forth in order to provide a more thorough understanding of the claimed subject matter. However, it will be apparent to one having ordinary skill in the art that the embodiments described may be practiced without these specific details. In other instances, well-known features have not been described in detail to avoid unnecessarily complicating the description.

Embodiments described herein generally relate to on-the-fly polymer quality testing, which may be used to ensure the quality of polymer solutions passing through a well injection system, including through porous medium of a near-wellbore formation. On-the-fly polymer quality testing according to embodiments disclosed herein may be performed prior to injection of the polymer into a wellhead, e.g., in an injection system at the surface of a well. For example, a testing assembly may be assembled along a flow line fluidly connecting an injection pump to the wellhead, where a polymer solution may be directed from the flow line and into the testing assembly to test the polymer quality in the fluid.

Polymer macromolecules in solution may be subject to mechanical degradation when flowing through various types of apparatuses (e.g., an injection pump, valves, chokes, pipeline connections, and/or a static mixer) and through porous medium in formations (e.g., in the near-wellbore formation) during injection from surface equipment into a well, such as in a polymer flooding operation or other injection operation. Testing assemblies and methods disclosed herein provide a way to test the effects of the injection operation on the quality of a polymer solution. Thus, such testing may be performed to determine if or how much the polymers degrade through the tested apparatuses and to assure the success of the injection operation (e.g., polymer flooding operation).

Testing assemblies disclosed herein may include a long bypass line that has a device base integrated along the bypass line. The device base may act as a universal component receptacle, where various types of apparatuses, such as valves, chokes, core sample holders, and static mixers, may be removably installed in the device base. When installed in a device base, an apparatus may provide a continuous flow path through the bypass line. In other words, an apparatus may be removably installed in a device base, such that when installed, a fluid may flow along a continuous flow path formed through both the bypass line and the apparatus, from an upstream portion of the bypass line, through the apparatus, and to a downstream portion of the bypass line.

When a polymer solution flows through an apparatus installed in the device base, the apparatus may agitate, grind, extrude, or exert other shearing forces on polymers in the solution, which may break the polymer molecule and cause mechanical degradation of the polymer. Such effects may be determined by testing the quality of the polymer solution after flowing through the apparatus. In other words, an apparatus may be removably installed in a device base of a testing assembly, and polymer quality of a fluid flowing through the installed apparatus may be tested in order to determine the effects on a polymer flowing through the apparatus. The polymer quality of the fluid may be tested from a testing site provided along the device base and/or the bypass line in a testing assembly, where a sample of the fluid may be taken to have one or more of its properties measured. While various testing procedures may be used to test the polymer quality in a fluid from a testing site, viscosity testing is described herein as an example of a way to evaluate polymer quality. For example, viscosity may be dependent on a molecular weight distribution of a polymer in solution. Correlations made between a polymer solution viscosity and the polymer's molecular weight or chain length may be used to determine an amount of polymer degradation occurring in the polymer solution from an initial viscosity of the polymer solution.

Figure 1:
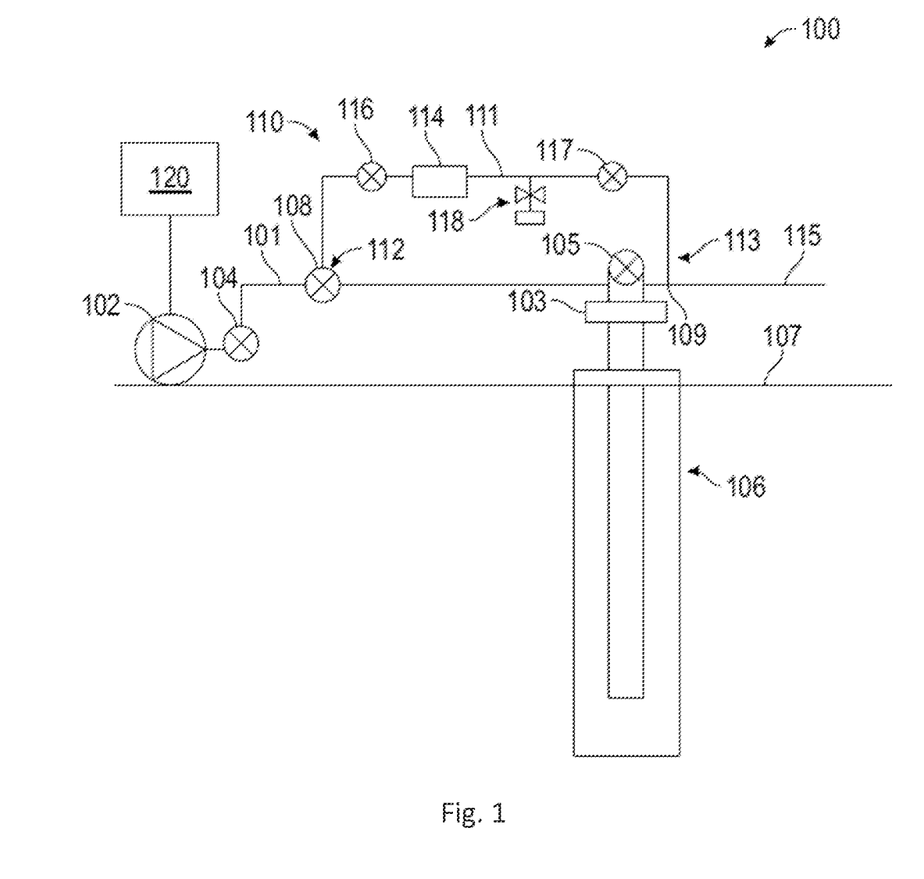
FIG. 1 shows an example of an injection system with a testing assembly according to embodiments of the present disclosure.

FIG. 1 shows an example of a system 100 using a testing assembly 110 according to embodiments of the present disclosure. The system includes a flow line 101 fluidly connecting one or more injection pumps 102 to a wellhead 103 on a well 106, where a fluid is pumped from an injection tank 120 (or other fluid source) to the well via the injection pump 102. The flow line 101 may be a pipe (e.g., a steel pipe) having various valves and/or other flow control devices provided along the length of the flow line 101, which is used to control the flow of a fluid through the flow line 101. For example, a flow line valve 104 is provided along the flow line 101, which allows or prevents fluid flow between the wellhead 103 and the injection pump 102. Additionally, the flow line 101 is connected to the wellhead 103 via a wellhead valve 105, which may be opened to allow fluid flow (or closed to prevent fluid flow) into or out of the wellhead 103. The wellhead valve 105 may be provided as part of the wellhead 103 (e.g., on a Christmas tree). In the embodiment shown, the flow line 101 is used to inject fluid into the well 106, for example, in a chemical flooding operation (e.g., polymer flooding, surfactant-polymer flooding, alkaline-surfactant-polymer flooding) of the well 106.

Wellheads 103 may have multiple valves and multiple flow lines connected to the wellhead 103 to control the flow of fluids into and out of the well 106. For example, in the embodiment shown in FIG. 1, a production line 115 is also connected to the wellhead 103, where the production line 115 is used for directing fluids produced from or exiting the well 106 to a location at the surface 107 of the well 106. In some embodiments, the production line 115 may be a disposal line, where fluid that was injected into the well 106 may be directed through the production line 115 after returning to the surface and being ejected from the well 106. One or more different wellhead valves may be used to control the flow of fluid from the well to the production line 115, where such valves may be referred to as production line valves.

A testing assembly 110 according to embodiments of the present disclosure is connected at a first connection end 112 to the flow line 101 between the flow line valve 104 and the wellhead valve 105. Thus, closure of the flow line valve 104 prevents fluid flow from a fluid source (e.g., tank 120) to the testing assembly 110. The testing assembly 110 is connected at the first connection end 112 to the flow line 101 via a flow divider valve 108. The flow divider valve 108 is positioned along the flow line 101 between the injection pump 102 and the wellhead 103 and may be used to divert the flow of fluid from the flow line 101 to the testing assembly 110. For example, the flow divider valve 108 may be a ball valve or other three-way valve, which in a first position, may close fluid flow to the flow line 101 and open fluid flow to the testing assembly, and in a second position, may open fluid flow to the flow line 101 and close fluid flow to the testing assembly.

According to embodiments of the present disclosure, a testing assembly 110 includes a bypass line 111 having a first connection end 112 and a second connection end 113 at opposite axial ends of the bypass line 111. Pipe used to form the bypass line 111 may be made of steel and/or other material designed to resist corrosion from an anticipated fluid flowing therethrough. In some embodiments, the bypass line 111 may have an inner diameter ranging from a lower limit selected from 0.5 inch, 1 inch, or 2 inches to an upper limit selected from 2 inches, 5 inches, or more, where any lower limit may be used in combination with any upper limit. For example, a pipe having a common inner diameter of 1.5 inches may be used to form the bypass line 111. In some embodiments, the bypass line 111 may have a length (measured from the first connection end 112 to the second connection end 113) that is greater than 15 meters, greater than 50 meters, or greater than 70 meters, depending, for example, on the system 100 the testing assembly 110 is assembled to.

The bypass line 111 extends from the flow divider valve 108 to a connection 109 to the production line 115, where the connection 109 is located downstream from the wellhead 103. The connection 109 may be at a valved junction (e.g., via a ball valve or other three-way valve) or at a pipe junction without a valve.

A device base 114 is positioned along the bypass line 111, for example, along a central portion of the bypass line 111. An upstream valve 116 is positioned along the bypass line 111 between the device base 114 and the first connection end 112, and a downstream valve 117 is positioned along the bypass line 111 between the device base 114 and the second connection end 113 of the bypass line. In such manner, the device base 114 is positioned along the bypass line 111 between the upstream valve 116 and the downstream valve 117.

Additionally, the testing assembly 110 may have a testing site 118 provided along the bypass line 111 or with the device base 114. In the embodiment shown in FIG. 1, the testing site 118 is provided along the bypass line 111, between the device base 114 and the downstream valve 117. The testing site 118 includes a sampling outlet provided in the bypass line 111, which may be selectively opened and closed to release an amount of fluid from the bypass line 111 for testing. In some embodiments, the testing site 118 includes a sampling line fluidly connected to the bypass line 111, where fluid may be flowed from the bypass line 111 through the sampling line to be tested. A sampling valve, such as a pressure relief valve, may be provided at a sampling outlet or along a sampling line to selectively allow fluid to drain from the bypass line 111 and be tested.

By providing a testing site 118 along a testing assembly 110 fluidly connected to and branched off a flow line 101, fluid from the flow line 101 may be rerouted to the testing assembly 110 and tested at the testing site 118 offline from operations using the flow line 101 (e.g., by closing one or more valves along the flow line 101 and/or bypass line 111). Additionally, by using methods disclosed herein for testing fluid from a testing assembly, unwanted mechanical degradation of polymers in the fluid may be minimized while taking samples of the fluid for testing. For example, in some embodiments, fluid may be sealed in the bypass line 111 (e.g., by closing valves around and/or along the bypass line), a sample of the fluid may be drained from a sampling outlet provided along the bypass line 111 at a location downstream from the device base 114, and the viscosity of the sample may be measured (e.g., using a viscometer). Sample testing may be done on site at the testing site 118, or a fluid sample collected from the testing site 118 may be brought to a laboratory or other off-site testing equipment for fluid testing.

Figure 2:
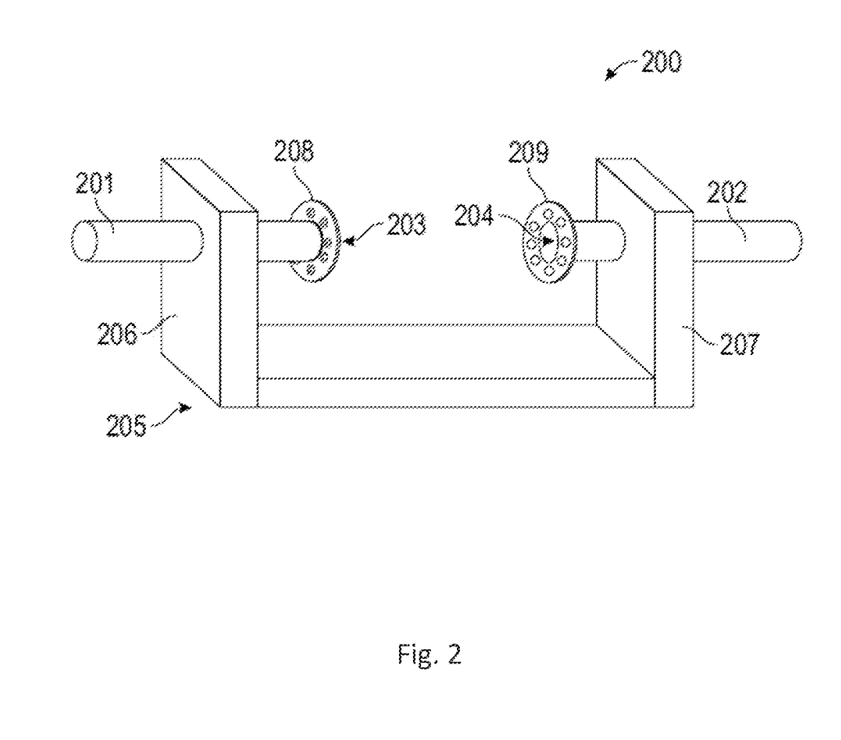
FIG. 2 shows an example of a device base according to embodiments of the present disclosure.

Referring now to FIG. 2, FIG. 2 shows an example of a device base 200 that may be used in a testing assembly according to embodiments of the present disclosure. The device base 200 is connected to and forms a part of a bypass line (e.g., 111 in FIG. 1) via a first bypass connection 201 and a second bypass connection 202. The first bypass connection 201 is connected to an upstream portion of the bypass line and the second bypass connection 202 is connected to a downstream portion of the bypass line, for example, using pipe connections (e.g., clamps or flanged connections). The device base 200 further includes a first opening 203 to the bypass line, where the first opening 203 is fluidly connected to the first bypass connection 201, and a second opening 204 to the bypass line, where the second opening 204 is fluidly connected to the second bypass connection 202. For example, in the embodiment shown in FIG. 2, the first and second bypass connections 201, 202 are pipe segments, where one axial end of each pipe segment is connected to the bypass line and the opposite axial end provides the openings (first and second openings 203, 204) to the bypass line.

The device base 200 may further include a support structure 205, which is used to support at least one of the first and second openings 203, 204. For example, in some embodiments, a support structure may be a single piece component having two or more arms, brackets, or other support element that may support or hold the first and second openings 203, 204 in a position relative to each other. In some embodiments, such as shown in FIG. 2, a support structure 205 includes two or more support elements 206 assembled to a base 207, where the support elements 206 hold the first and second openings 203, 204 in a position relative to each other. Various types and geometries for the support structure 205 may be envisioned. In some embodiments, the support structure 205 holds the first and second openings 203, 204 in a position relative to each other where the first and second openings 203, 204 are in axial alignment, such as shown in FIG. 2. In some embodiments, a support structure holds the first and second openings 203, 204 in a position where they are axially offset.

According to embodiments of the present disclosure, a removable apparatus may be installed in the device base 200 to fluidly connect the first opening 203 to the second opening 204. Connection elements 208, 209 are connected around the first and second openings 203, 204, or connection elements may be integrally formed around the first and second openings 203, 204, to connect the first and second openings 203, 204 to a removable apparatus. For example, as shown in FIG. 2, connection elements 208, 209 are flanges provided around the first and second openings 203, 204.

Removable apparatuses may include various types of components to be tested for determining their effects on degradation of polymers in a fluid flowing through the component. For example, removable apparatuses may include valves, e.g., a gate valve, ball valve, choke valve, globe valve, check valve, plug valve, butterfly valve, or torque valve, a static mixer, a core holder assembly, or a choke. Removable apparatuses may also include high pressure apparatuses, for example, apparatuses capable of holding a pressure up to about 2,000 psi.

According to embodiments of the present disclosure, a removable apparatus may be a core holder assembly that includes a core sample fitted inside a core holder body. The removable apparatus may have a flow path formed therethrough that fluidly connects with the flow path formed through a device base in which the removable apparatus may be installed. The flow path formed through the removable apparatus may have the same or approximately the same diameter as the flow path formed through the device base, e.g., to minimize pressure fluctuations of fluid flowing therethrough. The removable apparatus may also include one or more annular components used to hold the core sample in an axial position along the flow path, where at least some of the annular components may each have coaxially aligned passages forming the flow path through the removable apparatus. According to embodiments of the present disclosure, a core sample may be fitted inside the removable apparatus such that exposed portions of the core sample interfacing the flow path may have an area equal to (or approximately equal to) the cross-sectional area of the flow path. For example, a core sample may be held within a removable apparatus in a configuration where an exposed surface of the core sample interfacing a flow path in the removable apparatus has a diameter equal to the diameter of the flow path formed through the removable apparatus.

Figure 3A:
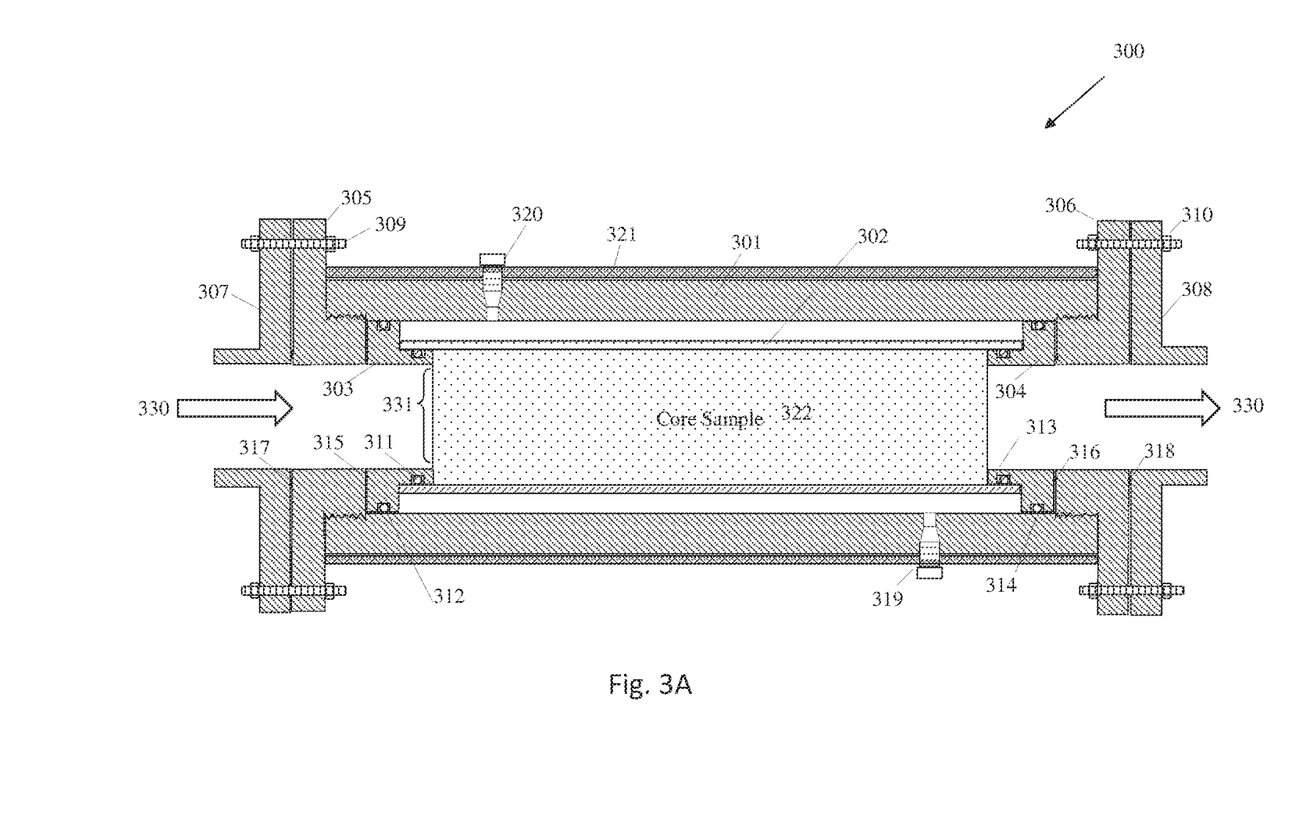
FIG. 3A shows a cross-sectional view of a core holder assembly according to embodiments of the present disclosure.
Figure 3B:
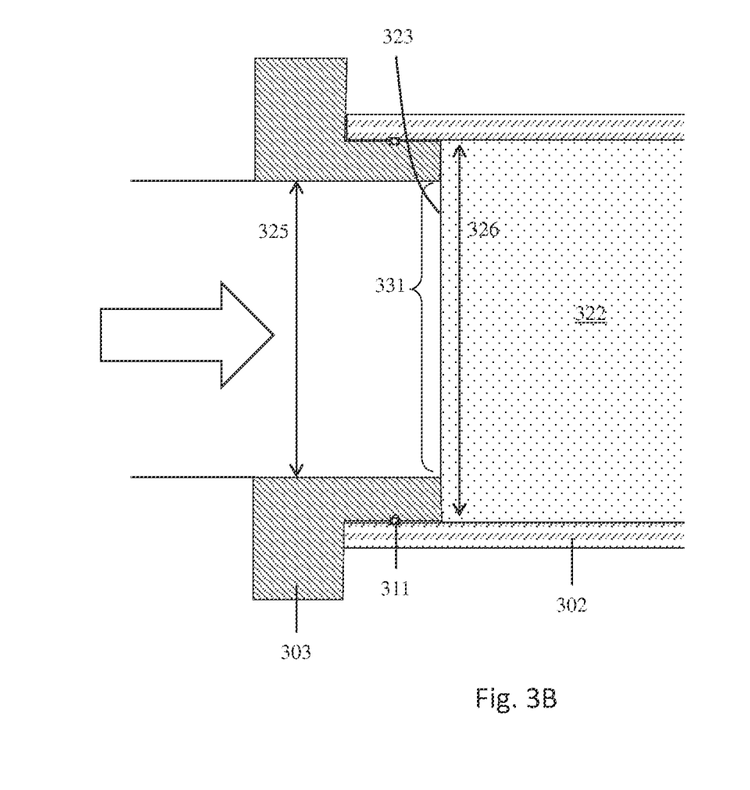
FIG. 3B shows a zoomed in cross-sectional view of an end plug positioned against an end surface of a core sample.
Figure 3C:
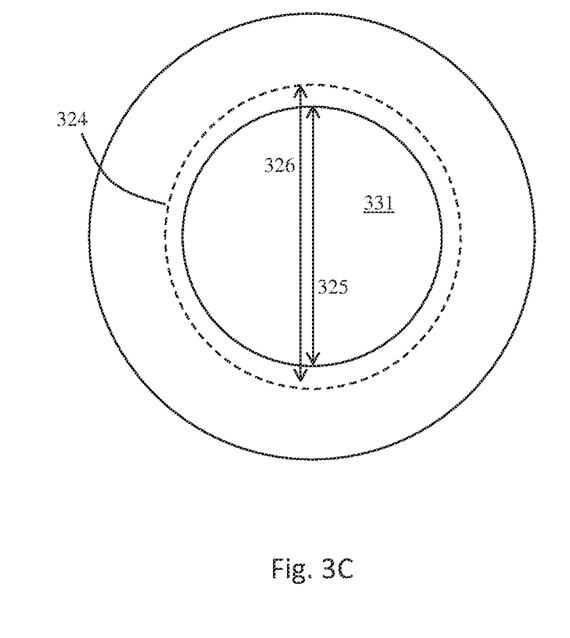
FIG. 3C shows a front view of the end plug positioned next to the core sample of FIG. 3B.

Referring now to FIGS. 3A-C, FIGS. 3A-C show an example of a removable apparatus 300 that is a core holder assembly, which may be used in testing the quality of a solution after it passes through a core sample. The removable apparatus 300 includes a core holder body 301 and a core sample assembly fitted inside the core holder body 301. The core sample assembly comprises a core sample 322 and a sleeve 302 fitted around the core sample 322.

The core sample assembly is fitted inside the core holder body 301 such that the core sample 322 is arranged along a flow path 330 formed through removable apparatus 300. The flow path 330 is formed through passages of annular components (discussed in more detail below) that are used to hold the core sample 322 in an axial position in the core holder body 301 and/or to connect the removable apparatus 300 to a device base. Additionally, the removable apparatus 300 is configured to hold the core sample 322 along the flow path 330 such that end surfaces the core sample 322 interface with the flow path 330 at exposed portions 331 of the core sample 322. The exposed portions 331 of the core sample 322 that interface the flow path 330 may have a diameter equal to the diameter of the flow path 330 through the removable apparatus 300 (e.g., including the inner diameter of connection ends of the removable apparatus 300). In some embodiments, the exposed portions 331 of the core sample 322 have a diameter equal to the inner diameter of the openings (e.g., openings 203, 204) to the bypass line that the removable apparatus 300 is connected to.

According to embodiments of the present disclosure, a core sample assembly may be sealed to an inner surface of the core holder body 301. For example, after the core sample 322 is inserted inside the sleeve 302 to form a core sample assembly, the sleeve 302 is sealed to an inner surface of the core holder body 301 at opposite axial ends of the sleeve. In the embodiment shown in FIG. 3A, the sleeve 302 is sealed to the core holder body 301 using first end plug 303 and second end plug 304. The end plugs 303, 304 each have an annular shaped body and may be positioned at opposite ends of the core sample 322, such that the annular body of the end plugs 303, 304 may interface with a perimeter portion of the core sample end surfaces, thereby leaving exposed portions 331 of the opposite end surfaces of the core sample 322 to interface with the flow path 330 formed through the removable apparatus 300. The end plugs 303, 304 may be held within the core holder body 301 via a first flanged stopper 305 and a second flanged stopper 306 positioned at opposite axial ends of the core holder body 301. The first and second flanged stoppers 305, 306 also each have a generally annular shaped body. The first and second flanged stoppers 305, 306 are coaxially positioned with the end plugs 303, 304 such that the flow path 330 is formed through the first flanged stopper 305, the first end plug 303, the second flanged stopper 306, and the second end plug 304.

In some embodiments, other annular-shaped elements may be used to seal a sleeve of a core sample assembly to the core holder body and/or hold the core sample in an axial position in the core holder body. For example, in some embodiments, a flanged stopper and an end plug may be integrally formed as one annular component. In some embodiments, a sleeve may have one or more annularly shaped protrusions formed at an axial end of the sleeve, which may be used to hold a core sample in an axial position and/or seal the sleeve to the inner surface of the core holder body. In such embodiments, the annularly shaped protrusion(s) of the sleeve may act as an end plug.

End plugs may be fitted with at least one o-ring to seal surfaces of the end plug to adjacent components. For example, FIG. 3A shows a first end plug 303 fitted with a sleeve o-ring 311 and a holder o-ring 312 and a second end plug 304 fitted with a second sleeve o-ring 313 and a second holder o-ring 314. The first and second sleeve o-rings 311, 313 may be used to seal the end plugs 303, 304 to the sleeve 302, while the first and second holder o-rings 312, 314 may be used to seal the end plugs 303, 304 to the core holder body 301.

According to embodiments of the present disclosure, a core sample assembly including a core sample and a sleeve may be coaxially assembled in a core holder body such that a confining annulus is formed between the sleeve and the core holder body. A confining annulus may be formed between a core sample assembly and a core holder body, for example, by using annular spacers or a core sample assembly sleeve that has integrally formed spacing features. In some embodiments, end plugs may be used to provide an annulus spacing between a core sample assembly and a core holder body. For example, as shown in FIG. 3A, the end plugs 303, 304 have an annular-shaped body with a shelf portion that extends in a radially outward direction from a core holding portion, where the shelf portion contacts the inner surface of the core holder body 301. In such manner, the shelf portion of the end plugs 303, 304 act as a spacer between the core sample assembly and the core holder body 301. Confining fluid may be introduced into the confining annulus via a first port 319 for confining pressure, and confining fluid may be drained from the confining annulus via a second port 320. The amount of confining fluid contained in the confining annulus may be controlled by opening and closing the first and second ports 319, 320 to provide a selected confining pressure. For example, in some embodiments, a confining pressure may be selected to be within a downhole pressure range (e.g., between 2,000 psi and 35,000 psi) to simulate downhole conditions. In some embodiments, a single port may be provided to fluidly connect a confining fluid with a confining annulus in the removable apparatus, where the amount of confining fluid through the single port may be regulated to provide a selected confining pressure in the removable apparatus.

Additionally, according to embodiments of the present disclosure, a heating jacket 321 may be provided around the core holder body 301. The heating jacket 321 may heat the interior of the core holder body (and thus a core sample assembly held inside the core holder body) to a selected testing temperature. According to embodiments of the present disclosure, a testing temperature may be selected to be within a downhole temperature range (e.g., between 100° C. and 350° C.) to simulate downhole conditions.

The removable apparatus 300 may be connected to a device base 200 via a flange connection. For example, in the embodiment in FIG. 3A, connection elements to the openings of a device base include a first flange connection 307 and a second flange connection 308. The first flange stopper 305 of the removable apparatus 300 may be connected to the first flange connection 307 of the device base and the second flange stopper 306 of the removable apparatus 300 may be connected to the second flange connection 308 using one or more connector. For example, in the embodiment of FIG. 3A, the flange stoppers 305, 306 may be connected to the flange connections 307, 308, respectively, via multiple connectors. The connectors may be one or more bolts 309 with nuts 310. The first flange connection formed between the first flanged stopper 305 and the first flange connection 307 may be sealed with a first flange gasket 317. The second flange connection formed between the second flanged stopper 306 and the second flange connection 308 may be sealed by a second flange gasket 318.

According to embodiments of the present disclosure, the axial length of the removable apparatus 300 may be designed to correspond with the axial length between the connection elements 307, 308 to the openings of a device base (e.g., device base 200 in FIG. 2). For example, a core holder body and flange stoppers may be designed to have a total axial length, when assembled together, that approximately equals the axial length between opposite connection elements of the openings to a device base. In some embodiments, when an axial length of a removable apparatus is less than the axial length between the openings of a device base, bridge pieces, such as flanged pipe segments, may be provided between a connection element (e.g., 307, 308 in FIG. 3A) of a device base opening and a connection element (e.g., 305, 306) of a removable apparatus in order to maintain the flow path between the device base and the removable apparatus.

Core samples 322 according to one or more embodiments may be obtained from a coring process to extract a segment of a downhole formation. A core sample obtained from a coring process may be shaped and sized to fit within a removable apparatus. For example, in some embodiments, a coring drill may remove a core sample directly from a downhole formation having a size and shape that corresponds with the size and shape of the sleeve in a removable apparatus. In some embodiments, a core sample removed from a downhole formation may be cut at the surface to have a selected size and shape. In some embodiments, when a core sample from a formation is extracted having a size that is smaller than the designed size to fit within a removable apparatus, one or more spacers may be provided in the removable apparatus to allow the core sample to be sealed within the flow path formed through the removable apparatus. A core sample may be removed from a downhole formation (e.g., from a near wellbore formation) that is representative of a target formation the testing fluid is designed to enter.

The core sample 322 may be saturated in a drilling fluid or an aqueous medium. The aqueous medium may be water, brine, or an aqueous fluid comprising additives known for use in oilfield applications.

Sleeves 302 according to one or more embodiments may be made of rubber and/or other inert polymer material. The sleeve 302 may comprise a rubber having a hardness of from 50-90 Shore A. Rubber forming the sleeve 302 may also have a temperature resistance from −20° C. to 200° C. An example of a rubber that may form the sleeve 302 is Viton™ rubber. The core sample assembly is formed by inserting a core sample 322 into a sleeve 302. When the sleeve 302 is fitted around the core sample 322, the sleeve 302 extends around the entire side surface of the core sample 322, leaving the opposite end surfaces of the core sample 322 exposed. In the embodiment shown, the sleeve 302 extends an axial length greater than the core sample 322, such that the opposite ends of the rubber sleeve 302 extend axially outwardly from the opposite ends of the core sample 322, thereby forming lip portions of the sleeve. The sleeve 302 may be sized to fit around the core sample 322 such that the sleeve 302 does not need to be stretched or cut for fitting. In one or more embodiments, an additional metal connection, such as a circle clamp, may be used to fit the sleeve 302 around the core sample 322.

The first end plug 303 and the second end plug 304 may be fitted at the opposite ends of the core sample adjacent to both the end surfaces of the core sample 322 and the lip portions of the rubber sleeve 302. In alternative embodiments, the end plugs 303 and 304 may be integrally formed with the sleeve 302. The end plugs 303, 304 are sized/shaped and positioned to both prevent axial movement of the core sample 322 in the removable apparatus 300 and to maximize the interface area between the flow path formed through the device base and the end surfaces of the core sample 322.

For example, FIG. 3B and FIG. 3C show zoomed in views of the first end plug 303 positioned against a first end surface 323 of the core sample 322, as shown in FIG. 3A. The first end plug 303 has an annular body with a passage having an inner diameter 325. The inner diameter 325 of the end plug 303 may be equal to one or both of the diameter of the flow path formed through the removable apparatus connection elements (e.g., the first and second flanged stoppers 305, 306) and the diameter of the flow path formed through the device base (e.g., 200 in FIG. 2) in which the removable apparatus 300 is installed. Additionally, as the end plug 303 is adjacent the end surface 323 of the core sample 322, the passage through the end plug 303 defines the exposed portion 331 of the end surface 323.

In the embodiment shown, the core sample 322 has a diameter 326 that is greater than the end plug inner diameter 325 (and thus greater than the flow path diameter), such that a portion of the end plug overlaps with a perimeter 324 of the core sample end surface 323. According to embodiments of the present disclosure, a core sample may have a diameter ranging, for example, between about 2 to 10 percent larger than the inner diameter of the end plug positioned adjacent the core sample. In some embodiments, the flow path created by the inner diameter of the end plug is at least 90 percent of the diameter of the end surfaces of the core sample 322. In such manner, the end plugs maintain the flow path from the device base through the core sample 322 while also preventing axial movement of the core sample 322.

Additionally, in the embodiment shown in FIGS. 3A-C, the end plugs 303, 304 have a sleeve portion positioned adjacent to the end surface 323 of the core sample 322. As shown in FIG. 3A, the sleeve portion of an end plug 303 may have an outer diameter substantially equal to the diameter 326 of the core sample 322, such that a sleeve 302 having a uniform inner diameter may extend around both the core sample 322 and the sleeve portion of the end plug 322. In such manner, the sleeve 302 may keep the end plug 303 coaxially aligned with the core sample 322.

The first sleeve o-ring 311 and first holder o-ring 312 may be fitted onto the first end plug 303, and the second sleeve o-ring 313 and second holder o-ring 314 may be fitted onto the second end plug 304 prior to seating the first end plug 303 and second end plug 304 in the sleeve 302.

The core sample 322 and sleeve 302 may be slid into the core holder body 301. The first end plug 303 and second end plug 304 may then be slid into opposite axial ends of the core holder body and sleeve. Optionally, a first end o-ring 315 and second end o-ring 316 may be placed into the core holder body 301 at each axial end. The first flanged stopper 305 and second flanged stopper 306 may then be threaded onto the core holder body 301 to seat onto the first end o-ring 315 and second end o-ring 316 or directly onto the first end plug 303 and second end plug 304. The core holder body 301 may be manufactured from a reinforced material such as stainless steel 316L, Hastelloy®, Monel®, titanium, Inconel®, or other suitable materials. In particular embodiments, the core holder body 301 may have a hollow cylindrical shape with an inside diameter ranging from about 2 to 7 inches. The o-rings may be produced from a rubber such as fluorocarbon (e.g., Viton™), nitrile (Buna), silicone, neoprene, ethylene-propylene (EPDM), and polytetrafluoroethylene (PTFE) (Teflon™), for example.

The removable apparatus 300 may be mounted onto a device base (e.g., device base 200 in FIG. 2) by a flange connection using bolts and nuts. The flange connection may be sealed with a flange gasket in-between the flange connection to prevent leaking. For example, the first flange connection is formed by contacting the first flanged stopper 305 with a flange gasket 317, which is contacted on the opposite side with the first flange connection 307. The connection is fastened and maintained via connectors, which may be for example bolts 309 and nuts 310. The second flange connection is formed by contacting the second flanged stopper 306 with the second flange gasket 318, which is contacted on the opposite side with the second flange connection 308. The connection is fastened and maintained via connectors, which may be for example bolts 309 and nuts 310.

The core holder body 301 is provided with a first port 319, which may be connected to an injection pump, and a second port 320, which may be connected to a valve. The injection pump and valve may be operated in conjunction to provide confining pressure around the core sample.

A hydraulic oil or water may be pumped into the injection pump port 319 to fill the confining annulus inside the core holder body 301, and then the confining pressure port valve may be closed at a target confining pressure to firmly hold the core sample 322 under the confining pressure.

A heating jacket used to apply and maintain a target temperature around the core sample may be placed around the core holder body or assembly. The removable apparatus 300 as described above may be used to assess the effects of pumping a fluid through a subterranean formation by analyzing properties of the fluid before and after passing through a core sample 322 representative of the subterranean formation loaded in the removable apparatus 322. Fluid to be injected into a subterranean formation may be, at least partially, diverted through a bypass line (e.g. 111 in FIG. 1) which is fluidly connected to the device base (e.g. 200 in FIG. 2) via a first bypass connection (e.g. 112 in FIG. 1; 201 in FIG. 2) and a second bypass connection (e.g. 113 in FIG. 1; 202 in FIG. 2).

Figure 4:
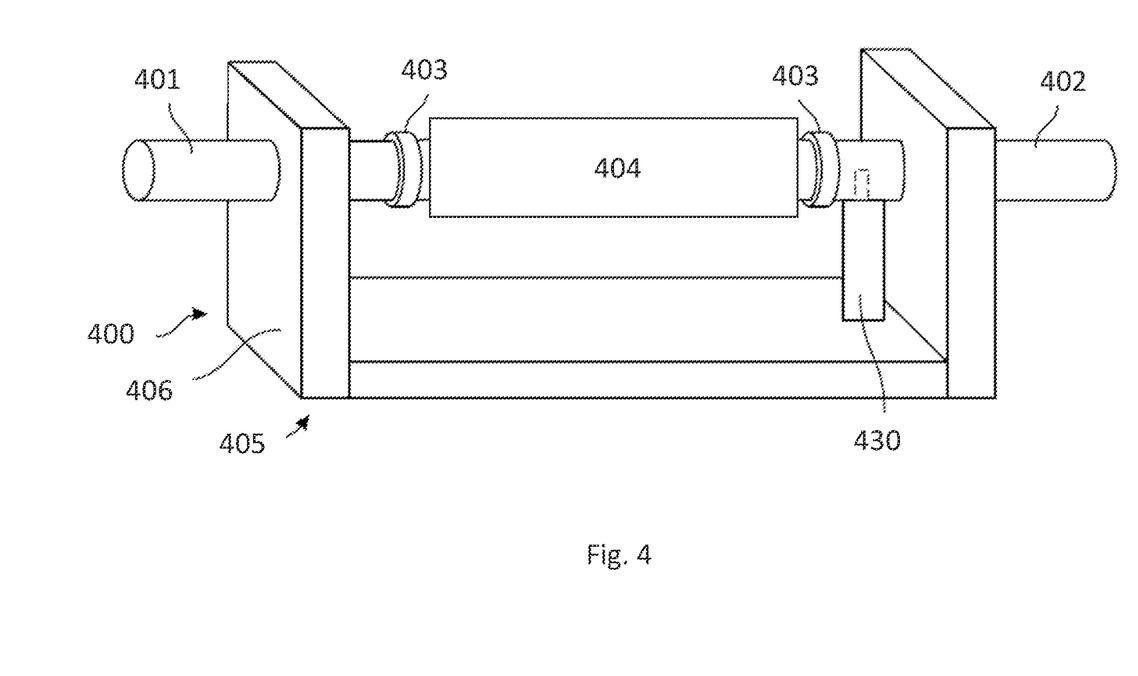
FIG. 4 shows an example of a removable apparatus installed in a device base according to embodiments of the present disclosure.

Referring now to FIG. 4, according to embodiments of the present disclosure, a removable apparatus 404 is installed in a device base 400, where the removable apparatus 404 is a core holder assembly, such as the removable apparatus 300 shown in FIGS. 3A-C. However, in contrast to the embodiment shown in FIG. 3A, the removable apparatus 404 is connected to the openings of the device base 400 via a clamped connection 403. One skilled in the art may appreciate that various types of connections may be used to connect a core holder assembly removable apparatus to a device base, where a substantially uniform flow path diameter may be maintained through the device base and the removable apparatus.

A viscometer 430 is provided at a testing site along the device base 400 to measure the viscosity of fluid flowing through the device base 400, after the fluid flows through a core sample (e.g., 322 in FIGS. 3A-C) in the removable apparatus 404, forming a testing assembly. Testing assemblies may include a removable apparatus according to the present disclosure and at least one testing device. A testing device may be any device or apparatus for measuring a property of the fluid which is passed through the flow path of the bypass line 111 which is fluidly connected to the removable apparatus 404 via the first and second bypass connections 401 and 402. For example, in the embodiment shown, a viscometer 430 is provided with a second bypass connection 402 of the device base 400. The viscometer 430 may be an in-line type viscometer, which may be inserted partially into the flow path through the second bypass connection 402 to measure the viscosity of fluid flowing therethrough. In other embodiments, a different type of testing device may be provided with the device base 400 to measure the quality of a polymer solution.

By providing a testing site (e.g., the location of viscometer 430) downstream of the removable apparatus (e.g., removable apparatus 404) being analyzed, the effect of the removable apparatus on the quality of the polymer solution flowing therethrough may be determined. However, in some embodiments, a viscometer (or other testing device) is fluidly connected to an upstream portion of the device base (e.g., first bypass connection 401). In some embodiments, a viscometer (or other testing device) is fluidly connected to both an upstream portion (e.g., first bypass connection 401) and a downstream portion (e.g., second bypass connection 402) of the device base 400, which may be used to provide polymer quality data for a polymer solution before and after flowing through the removable apparatus, and which may be compared to determine changes in the polymer solution resulting from the removable apparatus.

Testing assemblies according to embodiments of the present disclosure may be used in combination with fluid systems to provide polymer quality testing for conditions of interest for use with the fluid system. For example, testing assemblies disclosed herein may be used with a well system to test the effects on a polymer solution from different conditions of interest in the well system. Methods of testing the effects of flowing through a subterranean formation, or well system, on a polymer solution using testing assemblies according to embodiments of the present disclosure may include flowing the polymer solution through a removable apparatus in a testing assembly and measuring at least one property (e.g., viscosity) of the polymer solution after flowing through the removable apparatus.

A method may include providing a flow line fluidly connecting one or more injection pumps to a wellhead and a production line or discharge line fluidly connected to a downstream flow path in the wellhead. A testing assembly according to embodiments of the present disclosure may be connected to the flow line at a first connection end of the testing assembly and to the production line at a second connection end of the testing assembly. In such manner, a testing assembly (e.g., 110 in FIG. 1) may be assembled to an operational well system. By assembling a testing assembly to an operational well system (e.g., to a flow line connecting an injection pump to a wellhead), operational conditions such as the injection rate, pumping pressure, temperature, etc. of the well system may be used and replicated when testing a polymer solution through the testing assembly.

Testing assemblies that may be used in methods according to embodiments of the present disclosure may include, for example, a bypass line (e.g., 111 in FIG. 1) extending from a flow divider valve (e.g., 108 in FIG. 1) on the flow line (e.g., 101) to a downstream connection along the production line, where the downstream connection is downstream from the wellhead (e.g., 103 in FIG. 1). An upstream valve (e.g., 116 in FIG. 1) and a downstream valve (e.g., 117 in FIG. 1) may be positioned along the bypass line, and a device base (e.g., 114 in FIG. 1) may be positioned along the bypass line between the upstream valve and the downstream valve. The device base may provide a first opening to the bypass line and a second opening to the bypass line, where a removable apparatus may be installed in the device base and fluidly connect the first opening to the second opening of the bypass line. In such manner, a continuous flow path through the bypass line may be formed when a removable apparatus is installed in the device base. As discussed herein, a removable apparatus may be an apparatus having a fluid flow path formed therethrough and may have a functionality to direct fluid therethrough in a certain way.

For example, the removable apparatus may be the removable apparatus 300 shown in FIG. 3A. In such an embodiment, fluid may be flowed into the bypass line through a first opening to the bypass line and through the first bypass connection which is fluidly connected to the removable apparatus via the first flange connection 307 which is contacted by the first flanged stopper 305. The fluid may be flowed through the annulus of the first flanged stopper 305 and first end plug 303 and contact the exposed portion 331 of the end surface 323 of the core sample 322. The fluid is flowed through the core sample 322 to exit the opposite end of the core sample 322 and flow through the annulus of the second end plug 304, the second flanged stopper 306, and second flange connection 308. The fluid is then flowed out of the bypass line through the second opening to the bypass line.

When a testing assembly according to embodiments of the present disclosure is assembled to a flow line, a method may further include flowing a fluid through the flow line and the bypass line in the testing assembly to the production line, where the tested fluid may be discharged or reused. For example, a polymer solution may be pumped through the flow line using one or more injection pumps and directed to a bypass line in a connected testing assembly via a flow divider valve. An amount of the fluid may be pumped through the bypass line sufficient to flush the bypass line with the fluid. For example, at least 2 barrels of the fluid (e.g., between 2 and 5 barrels) may be flowed through the bypass line to flush the bypass line. Fluid may be flushed through the bypass line and into a fluidly connected production line (e.g., 115 in FIG. 1). Flushing the bypass line with a fluid prior to testing the fluid may be done to prevent remnants of other material in the bypass line from affecting the testing.

After flowing a fluid through the flow line and the bypass line in the testing assembly, an upstream valve and a downstream valve in the testing assembly may be closed to seal a portion of the fluid in a portion of the bypass line around the device base. In some embodiments, prior to closing the upstream valve and the downstream valve, the pumping rate of the fluid may be reduced and a wellhead valve (e.g., 105 in FIG. 1) to the wellhead may be closed to stop fluid flow into the wellhead.

After stopping the flow of fluid through the bypass line, a property of the fluid sealed in the bypass line may be measured. For example, according to embodiments of the present disclosure, a sample of the fluid may be drained from a sampling outlet provided along the bypass line between the device base and the downstream valve (downstream of the device base and installed removable apparatus). Once the sample of fluid is drained, a property of the fluid sample may be measured, such as the viscosity of the fluid sample. Other testing devices may be provided at a testing site downstream from the installed removable apparatus to test a property of fluid that flowed through the removable apparatus. Further, other methods may be used to measure a property of the fluid within the testing assembly, including methods that drain a fluid sample prior to testing and methods that measure a fluid property within the bypass line (without draining a fluid sample from the bypass line).

The measured property of the fluid may be used to determine a quality of polymers in the fluid. For example, the viscosity of a polymer solution may be measured at a testing site downstream from the removable apparatus installed in the testing assembly, where the viscosity may indicate an amount of polymer degradation occurring from the polymer solution flowing through the removable apparatus.

According to embodiments of the present disclosure, a measured viscosity of a polymer solution downstream from an installed removable apparatus may be compared with an initial viscosity of the polymer solution in order to determine an amount of polymer degradation resulting from its flow between the point where the polymer solution has the initial viscosity to the point where the polymer solution has the downstream viscosity measurement. In some embodiments, an initial viscosity may be determined prior to pumping the polymer solution from an injection tank to a well system via injection pumps. In some embodiments, an initial viscosity may be measured at a location along the testing assembly upstream from the removable apparatus (e.g., in an upstream portion of a bypass line, upstream from an installed removable apparatus).

By comparing a downstream measured viscosity of the polymer solution to an initial viscosity of the polymer solution, the degradation level of the polymer solution may be identified resulting from the flow of the polymer solution between a location where the polymer solution has the initial viscosity and the downstream location where the measured viscosity is taken. For example, in some embodiments, an initial viscosity of a polymer solution may be determined for the polymer solution in an injection tank. The polymer solution may then be pumped via injection pump(s) to a testing assembly, where a downstream viscosity may be measured after the polymer solution has flowed through an installed removable apparatus. In such embodiments, an amount of polymer degradation resulting from the polymer solution flowing from the injection tank to the removable apparatus may be determined by comparing the initial viscosity to the downstream viscosity.

In some embodiments, an initial viscosity of a polymer solution may be measured upstream of an installed removable apparatus in an upstream portion of a testing assembly, and a downstream viscosity of the polymer solution may be measured downstream of the installed removable apparatus in a downstream portion of the testing assembly. In such embodiments, an amount of polymer degradation resulting from the polymer solution flowing through the removable apparatus may be determined by comparing the initial viscosity to the downstream viscosity.

In some embodiments, a removable apparatus comprises a core holder assembly. In such embodiments, the flow of fluid through the bypass line flows through the core holder assembly and the core sample comprised therein. The properties of the fluid after flowing through the core sample, for example the viscosity, allow for the determination of the performance of the fluid after flowing through the wellbore formations from which the core sample was obtained. When the fluid is a polymer solution, the degradation of the polymer in the solution after use in the wellbore may be determined.

Thus, by using methods according to embodiments of the present disclosure to determine an amount of polymer degradation resulting from flow through a system, the strength of the polymer solution in the field may be identified, including identifying how well the polymer solution can hold different shears within a particular wellbore formation.

Additional examples of methods according to embodiments of the present disclosure are provided below.

Example 1

An example testing procedure according to embodiments of the present disclosure is provided below and described with respect to the system shown in FIG. 1. However, similar testing procedures may be performed on other systems having testing assemblies according to embodiments of the present disclosure.

A testing procedure for testing polymer quality of a polymer solution flowing through the well system 100 shown in FIG. 1 may include:
1) Open a flow line valve 104 (e.g., a production valve), which may allow the polymer solution to be pumped from a fluid source 120 via one or more injection pumps 102 through the flow line 101.
2) Open a flow divider valve 108 to divert flow from the flow line 101 to the bypass line 111 of a testing assembly 110.
3) Close a wellhead valve 105 to prevent fluid from an upstream portion of the flow line 101 from flowing to the wellhead 103.
4) Flush the bypass line 111 with the polymer solution (e.g., 2-5 barrels of the polymer solution), where the flushed polymer solution may be injected into the wellhead 103.
5) Reduce the pumping rate of the injection pump(s) 102 and close a production line 115 from the wellhead 103 (e.g., close a production line valve) at the same time.
6) Open wellhead valve 105 and close a downstream valve 117 in the testing assembly 110 at the same time in order to prevent the polymer solution from flowing from the bypass line 111 to the wellhead 103.
7) Close an upstream valve 116 in the testing assembly 110 in order to seal an amount of the polymer solution within the bypass line 111 between the upstream valve 116 and the downstream valve 117.
8) Release the pressure in the sealed portion of the bypass line 111 to 0 psi at a sampling point (testing site 118) and collect a sample of the polymer solution sample for viscosity measurement.

The sample viscosity measurement may be compared with an initial viscosity of the polymer solution (e.g., the viscosity of the polymer solution at the fluid source 120) to determine an amount of polymer degradation resulting from the flow of the polymer solution from the location of initial viscosity, through the removable apparatus, to the testing site 118.

Example 2: Polymer Injection in an Open Hole Completion Well

A core holder with a carbonate core plug of 1.5 inch in diameter and 1.5 inch in length was mounted in a core holder assembly at the device base. The confining pressure was set at 1500 psi using a hand pump. The temperature of the core holder was set to 95° C. A surfactant-polymer mixed solution in seawater with a concentration of 0.2% betaine-type surfactant and 0.2% sulfonated polyacrylamide respectively was injected into the core sample according to the general sampling procedure described above. Five barrels of surfactant-polymer mixed solution were pumped through the core holder assembly at 1.5 L/hr. The polymer solution samples are collected at the point before pumping the polymer solution and the viscosities are measured as Vpre. The polymer solution samples are collected at the downstream point according to the sampling procedure described above and viscosities are measured as $V_{aft}$. The fraction of polymer degradation caused by the flow in the porous media can be described as $(V_{pre}-V_{aft})/V_{pre}$. These results demonstrate Example 3: Polymer Injection in a Perforated Completion Well A core holder with a carbonate core plug of 1.5 inch in diameter and 1.5 inch in length was mounted at the device base. The confining pressure was set at 1500 psi using a hand pump. The temperature of the core holder was set to 95° C. A surfactant-polymer mixed solution in seawater at concentration of 0.2% and 0.2% respectively was injected into the core sample according to the general sampling procedure described above. Five barrels of surfactant-polymer mixed solution were pumped through the device at 1.0 L/hr. The polymer solution samples are collected at the point before pumping the polymer solution and the viscosities are measured as $V_{pre}$. The polymer solution samples are collected at the downstream point according to the sampling procedure described above and viscosities are measured as $V_{aft}$. The fraction of polymer degradation caused by the flow in the porous media can be obtained by the description above.

Although only a few example embodiments have been described in detail above, those skilled in the art will readily appreciate that many modifications are possible in the example embodiments without materially departing from this invention. Accordingly, all such modifications are intended to be included within the scope of this disclosure as defined in the following claims.

What is claimed:

1. A removable apparatus, comprising:
   a core holder body;
   a core sample assembly fitted inside the core holder body, the core sample assembly comprising:
     a core sample; and
     a sleeve fitted around the core sample, wherein the sleeve is sealed to an inner surface of the core holder body at opposite axial ends of the sleeve; and
   a first flanged stopper and a second flanged stopper positioned at opposite axial ends of the core holder body;
   wherein a flow path is formed through the first and second flanged stoppers and interfaces with opposite end surfaces of the core sample; and
   wherein the flow path has a diameter that is at least 90 percent of a diameter of the opposite end surfaces of the core sample.

2. The removable apparatus according to claim 1, wherein the sleeve is sealed to the inner surface of the core holder body using a first end plug and a second end plug positioned against the opposite end surfaces of the core sample.

3. The removable apparatus of claim 2, wherein the first end plug and the second end plug each have a passage with an inner diameter equal to a diameter of the flow path.

4. The removable apparatus of claim 2, wherein the first end plug and the second end plug are sealed against both the inner surface of the core holder body and a lip portion of the sleeve using o-rings.

5. The removable apparatus according to claim 1, further comprising a confining annulus formed between the sleeve and the inner surface of the core holder body, wherein the confining annulus is sealed at opposite ends using a first end plug and a second end plug.

6. The removable apparatus according to claim 1, wherein the core holder body further comprises a first port fluidly connected to a confining annulus formed between the core holder body and the sleeve.

7. An assembly, comprising:
a bypass line having a first connection end and a second connection end;
a device base positioned along the bypass line, wherein the device base comprises:
a first opening to the bypass line;
a second opening to the bypass line; and
a support structure supporting at least one of the first and second openings; and
the removable apparatus of claim 1 positioned in the device base.

8. The assembly of claim 7, wherein the first connection end is connected to a flow divider valve positioned along a flow line to an injection pump.

9. The assembly of claim 7, wherein the second connection end is connected to a production line, and wherein the production line is fluidly connected to a wellhead.

10. The assembly of claim 7, further comprising a sampling outlet provided along the bypass line between the device base and the second connection end.

11. A system, comprising:
a flow line fluidly connecting an injection pump to a wellhead;
a production line fluidly connected to the wellhead;
a flow divider valve positioned along the flow line between the injection pump and the wellhead;
a bypass line extending from the flow divider valve to a downstream connection to the production line;
an upstream valve and a downstream valve positioned along the bypass line;
a device base positioned along the bypass line between the upstream valve and the downstream valve, wherein the device base comprises:
a first opening to the bypass line;
a second opening to the bypass line; and
a support structure supporting at least one of the first and second openings; and
a removable apparatus installed in the device base fluidly connecting the first opening to the second opening, wherein the removable apparatus comprises:
a core holder body;
a core sample assembly fitted inside the core holder body, the core sample assembly comprising:
a core sample; and
a sleeve fitted around the core sample, wherein the sleeve is sealed to an inner surface of the core holder body; and
at least one first annular component and at least one second annular component positioned at opposite axial ends of the core holder body,
wherein a flow path is formed through the at least one first annular component and the at least one second annular component and interfaces with opposite end surfaces of the core sample.

12. The system of claim 11, wherein a bypass flow path formed through the first opening has a diameter equal to a diameter of the flow path formed through the at least one first annular component and the at least one second annular component.

13. The system of claim 12, wherein the core sample interfaces the flow path at exposed portions of opposite end surfaces, and wherein the exposed portions have a diameter equal to the diameter of the bypass flow path.

14. The system of claim 11, wherein the at least one first annular component comprises:
a first end plug interfacing a first end surface of the core sample; and
a first flanged stopper positioned adjacent to the first end plug opposite the core sample,
wherein the first flanged stopper is connected to the first opening of the bypass line.

15. The system of claim 11, further comprising a sampling line fluidly connected to the bypass line between the device base and the downstream valve.

16. The system of claim 11, wherein the removable apparatus is connected to the first opening and the second opening via flange connections.

17. A method, comprising:
providing a flow line fluidly connecting an injection pump to a wellhead;
providing a production line fluidly connected to the wellhead;
providing a testing assembly connected between the flow line and the production line, wherein the testing assembly comprises:
a bypass line extending from a valved connection on the flow line to a downstream connection to the production line;
a device base positioned along the bypass line, wherein the device base comprises:
a first opening to the bypass line; and
a second opening to the bypass line;
installing a removable apparatus in the device base, wherein the removable apparatus comprises:
a core holder body;
a core sample assembly fitted inside the core holder body, the core sample assembly comprising:
a core sample; and
a sleeve fitted around the core sample, wherein the sleeve is sealed to an inner surface of the core holder body; and
at least one first annular component and at least one second annular component positioned at opposite axial ends of the core holder body,
wherein the installing comprises connecting a first end of the removable apparatus to the first opening to the bypass line and connecting a second end of the removable apparatus to the second opening to the bypass line to fluidly connect the first opening to the second opening;
flowing a fluid through the flow line and the bypass line; and
testing a property of the fluid after it flows through the removable apparatus.

18. The method of claim 17, further comprising closing an upstream valve along the bypass line upstream from the device base and closing a downstream valve along the bypass line downstream from the device base to seal the fluid in a portion of the bypass line, where the testing is conducted while the upstream valve and the downstream valve are closed.

19. The method of claim 18, further comprising, prior to closing the upstream valve and the downstream valve, reducing a pumping rate of the fluid and closing a wellhead valve to stop fluid flow from the wellhead to the production line.

20. The method of claim 17, wherein the testing comprises:
- draining a sample of the fluid from a sampling outlet provided along the bypass line downstream from the removable apparatus; and
- measuring a viscosity of the sample of the fluid.

* * * * *